US007146030B2

(12) United States Patent
Vailaya et al.

(10) Patent No.: US 7,146,030 B2
(45) Date of Patent: Dec. 5, 2006

(54) SYSTEM AND METHODS FOR EXTRACTING SEMANTICS FROM IMAGES

(75) Inventors: Aditya Vailaya, Santa Clara, CA (US); Annette Marie Adler, Palo Alto, CA (US); Allan Kuchinsky, San Francisco, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 611 days.

(21) Appl. No.: 10/155,615

(22) Filed: May 22, 2002

(65) Prior Publication Data

US 2003/0219149 A1 Nov. 27, 2003

(51) Int. Cl.
G06K 9/00 (2006.01)
(52) U.S. Cl. ...................... 382/128; 345/440
(58) Field of Classification Search ........ 382/128–133, 382/134, 190; 600/352, 562, 425, 443; 435/6, 435/9, 69.1, 94.1, 447; 436/63, 74, 178, 436/519; 345/418, 440, 501–503, 522, 530, 345/650, 661
See application file for complete search history.

(56) References Cited

U.S. PATENT DOCUMENTS

| 5,522,022 | A | * | 5/1996 | Rao et al. ............... 345/440 |
| 5,544,654 | A | * | 8/1996 | Murphy et al. .......... 600/443 |
| 5,619,995 | A | * | 4/1997 | Lobodzinski ............ 600/425 |
| 6,031,930 | A | * | 2/2000 | Bacus et al. ............ 382/133 |
| 6,336,124 | B1 | * | 1/2002 | Alam et al. ............. 715/523 |
| 6,522,774 | B1 | * | 2/2003 | Bacus et al. ............ 382/133 |
| 6,762,025 | B1 | * | 7/2004 | Cubicciotti ............. 435/6 |
| 6,780,154 | B1 | * | 8/2004 | Hunt et al. ............. 600/446 |

OTHER PUBLICATIONS

Website: http://www.dcs.ed.ac.uk/home/mxr/gfx/utils-hi.html, entitled "The Graphics File Formats Page," dated May 14, 2002.
Website: http//www.faqs.org/faqs/graphics/fileformats-faq/part3/preamble.html, entitled "Graphics File Formats FAQ (Part 3 of 4): Where to Get File Format Specifications," dated May 14, 2002.
Website: http://transpath.gbf.de/, entitled "TRANSPATH Signal Transduclion Browser," BIOBASE dated May 22, 2002.
Website: http://www.gene-regulation.com/pub/databases.html, entitle"Gene Regulation," BIOBASE dated May 22, 2002.
Website: http//www.genome.ad.jp/kegg/kegg.html, entitled "KEGG: Kyoto Encyclopedia of Genes and Genomes," dated May 22, 2002.
Website: http://www.grt.kyushu-u.ac.jp/spad, entitled "SPAD Signal Pathway Database," dated May 22, 2002.
Website: http://www.bind.ca/index.phtml?page=databease, entitle"Biomolecular Interaction Network Database" dated May 22, 2002.
Website: http//www.ncbi.nlm.nih.gov/LocusLink/, entitled "LocusLink Introduction," dated May 22, 2002.
Website: http://www.empproject.com/terms/index1.shtml, entitled "EMP Project Terms of Use," dated Mar. 26, 2002.
Website: http://www.transfac.gbf.de/TRANSFAC/ entitle"TRANSFAC—The Transcription Factor Database" dated May 22, 2002.

* cited by examiner

Primary Examiner—Jingge Wu
Assistant Examiner—Abolfazl Tabatabai

(57) ABSTRACT

System, tools and methods for extracting the contents from a graphical image, such as the representation of a biological process, and converting the contents into a standardized, machine readable format. The standard format can be used to create editable graphical representations of images, such as biological models.

37 Claims, 4 Drawing Sheets

SYSTEM AND METHODS FOR EXTRACTING SEMANTICS FROM IMAGES

FIELD OF THE INVENTION

The present invention pertains to software systems and method supporting extraction of semantics from graphic images of biological models and for converting the semantics to a local format.

BACKGROUND OF THE INVENTION

The completion of mapping of the human genome in 2000, has led to an increased focus on functional genomics, i.e., extracting functional knowledge regarding various biological processes. Various experimental methods and tools are being invented to shed light into the functioning of processes within various organisms, with the final goal being to understand these in humans. A common way to represent the known functional biological knowledge is via pathway diagrams, cellular networks, and diagrams of biological and chemical models.

These representations are used to display information such as signal transduction pathways, regulatory pathways, metabolic pathways, protein-protein interactions, etc. These diagrams represent biological relationships (such as bind, cleave, inhibit, promote, catalyze, etc.) between entities (genes, proteins, mRNA, other molecules of interest) along with their localization within the cell, tissue, or organism. These visual representations are graphical in nature and are static images, i.e., they cannot be revised, supplemented or otherwise edited. Hence, they present the results for human visualization, rather than in a machine interpretable format.

Biologists are in need of tools that facilitate their use of biological models beyond the ability to simply visually compare such models with other information and data. There is a need for tools which would enable a researcher to not only view various biological models, but to also supplement, edit or otherwise modify these models in accordance with the researchers understandings gained from research done (e.g., comparison with local data) as well as from comparisons with other published data.

A number of biological model (e.g., KEGG, Transfac, Transpath, SPAD, Bind, etc.) databases have been developed (both public domain and proprietary) that allow users to query and download biological models of interest. However, as noted, the user can only view these biological models after downloading them, and can not add meaningful data or edits to a model given its static nature. Thus, it is cumbersome to import these diagrams, manually extract contents from them, and link the extracted information to other types of data (such as experimental data, scientific text, information about entities of interest, etc.).

Although there exists a great deal of research and development with regard to optical character recognition (OCR) and image processing, the present inventors are not aware of any tools that currently map standardized graphics in the biology domain to machine readable/interpretable format, and which use information from the standardized graphics to develop editable and modifiable views of the underlying biological models. The bulk of the focus in research in the OCR and image processing fields has been concentrated around scanners and other systems, with attempts being made to convert information present in paper form to a concise digital form. For example, the goal of these systems is to reduce the amount of space required to store the scanned document. An image of the page with text would require many orders more storage space than the ASCII representation of the text therein. Thus, these systems are faced with a very general problem, the scanned document may have any font, any combination of images and graphics, may not be properly oriented, etc. In other terms, the input to such systems may not be restricted.

U.S. Pat. No. 5,522,022 to Rao et al., discloses an image analysis technique which is generally applicable for analyzing images such as directed graphs, undirected graphs, trees, flow charts, circuit diagrams, and state-transition diagrams that show node-link structures. Because of its general applicability, the technique is designed to resolve ambiguity that exists across various types of graphical representations, e.g., labels resembling nodes or links, other characters or lines which may be confused with links or nodes, and the like. Because this technique does not begin with any predefined parameters with regard to an image type, it is geared toward resolving these ambiguities and identifying nodes and links that exist in a diagram. To do this, the technique first identifies "likely node-link data" indicating parts of an input image that are likely to contain a link and/or node. Likely node-link data are data from those parts of the image which satisfy a constraint on nodes and those parts which satisfy a constraint on links. The likely node-link data are then used to define constrained node-link data indicating subsets of the likely nodes and links that satisfy a constraint on node-link structures. The constrained node-link data are obtained by iteratively applying a link nearness criterion to the likely nodes and a node nearness criterion to the likely links until stability is reached. This approximation approach is necessitated by the lack of a standardized format of the images being processed, as well as the need to make the technique generally applicable to many types of graphical images.

There remains a need for tools and methods that efficiently facilitate the use of biological models beyond the ability to simply visually compare such models with other information and data, and which would enable a user to not only view various biological models, but to also supplement, edit or otherwise modify these models.

SUMMARY OF THE INVENTION

The present invention uses image processing and other information to extract contents from a static graphical representation of a biological process and converts the contents into a machine-readable format (referred to as the local format). Static images from multiple database sources can thus, be harmonized in a standard local format. The local format may be used to create editable/modifiable graphical representations of the various biological models.

A method of extracting semantics from a static graphic image of a biological model and for converting the static image to an editable biological model is described, including accessing stored information defining predefined constraints used to create the static image; identifying at least one entity or relationship represented in the static image, based upon the stored information; extracting information describing at least one entity or relationship; and converting at least a portion of the biological model to an editable, local format using the extracted information.

The predefined constraints may include site-specific vocabulary, assignments of different colors to entities and relationships, and/or assignments of different shapes to entities and relationships.

Image processing employed in the method may include one or more of the following techniques: color- and/or shape-processing, morphological analysis open/closed operators), connected component analysis, edge detection, detecting geometrical shapes, template matching, and detecting text in the image. Image processing may be applied to the entire static image or regions in the image.

Regions in the image may be pre-selected manually or automatically based on color-processing, shape-processing, and/or connected component analysis.

The static image may be digitally created or scanned from a paper source. The static image may be converted to a standard format prior to the identifying and extracting steps of the method. The standard format may be JPEG, PBM, GIF, TIFF or Bitmap, for example.

The method may further include: accessing an image map used to create the static image; identifying at least one entity or relationship represented in the static image, based upon information in the image map; extracting information describing at least one entity or relationship identified based upon the image map information; and converting at least a portion of the biological model to the editable, local format using the information extracted based upon the image map information. The image map may include HTML programming that is used in creating the static image.

The present invention further allows manual conversion of at least a portion of the biological model to an editable, local format.

Further, a method of extracting semantics from a static graphic image of a biological model and for converting the static image to an editable biological model is described to include accessing an image map used to create the static image; identifying at least one entity or relationship represented in the static image, base upon information in the image map; extracting information describing at least one entity or relationship; and converting at least a portion of the biological model to the editable, local format using the extracted information.

The static image may be digitally created or scanned from a paper source, and the method may further include the step of converting the static image into a standard format prior to the identifying and extracting steps.

Still further, the method may include: accessing stored information defining predefined constraints used to create the static image; identifying at least one entity or relationship represented in the static image, based upon the stored information; extracting information describing at least one entity or relationship, based upon the stored information; and converting at least a portion of the biological model to an editable, local format using the information that was extracted based upon the stored information.

Manual conversion of at least a portion of the biological model to an editable, local format may be performed.

OCR may be applied to text regions of the static image to convert the text to the local format.

A system for extracting semantics from a static graphic image of a biological model and for converting the static image to an editable biological model is described to include means for accessing stored information defining predefined constraints used to create the static image; means for identifying at least one entity or relationship represented in the static image, based upon the stored information; means for extracting information describing at least one entity or relationship; and means for converting at least a portion of the biological model to an editable, local format using the extracted information.

The system may further include means for converting the static image into a standard format prior to extracting semantics therefrom.

Still further, the system may include: means for accessing an image map used to create the static image; means for identifying at least one entity or relationship represented in the static image, based upon information in the image map; means for extracting information describing the at least one entity or relationship identified based upon the image map information; and means for converting at least a portion of the biological model to the editable, local format using the information extracted based upon the image map information.

Means for manually converting at least a portion of the biological model to an editable, local format may also be provided.

A system for extracting semantics from a static graphic image of a biological model and for converting the static image to an editable biological model is described to include: a database-specific content extraction module adapted to extract content from the static image based on predefined constraints specific to a database from which the static image originated; and a conversion module adapted to convert the extracted content to a local format used to create an editable biological map corresponding to the static image.

The system may further include an image mapping module adapted to extract content in or relating to the static image, based upon an image map, and input the extracted content from or relating to the static image to the conversion module.

Still further, the system may include an image preprocessing module adapted to convert the static image to a standard format, prior to further processing by the system.

A computer readable medium carrying one or more sequences of instructions from a user of a computer system for identifying data relevant to the context of a user's local data is described, wherein the execution of the one or more sequences of instructions by one or more processors cause the one or more processors to perform the steps of: accessing stored information defining predefined constraints used to create the static image; identifying at least one entity or relationship represented in the static image, based upon the stored information; extracting information describing the at least one entity or relationship; and converting at least a portion of the biological model to an editable, local format using the extracted information.

Execution of the medium may further cause the performance of converting the static image into a standard format prior to the identifying and extracting steps.

Still further, the execution of the steps of accessing an image map used to create the static image; identifying at least one entity or relationship represented in the static image, based upon information in the image map; extracting information describing at least one entity or relationship identified based upon the image map information; and converting at least a portion of the biological model to the editable, local format using the information extracted based upon the image map information may be performed.

A computer readable medium carrying one or more sequences of instructions from a user of a computer system for identifying data relevant to the context of a user's local data is described, wherein the execution of the one or more sequences of instructions by one or more processors cause the one or more processors to perform the steps of: accessing an image map used to create the static image; identifying at least one entity or relationship represented in the static image, base upon information in the image map; extracting information describing the at least one entity or relationship; and converting at least a portion of the biological model to the editable, local format using the extracted information.

These and other objects, advantages, and features of the invention will become apparent to those persons skilled in the art upon reading the details of the system and methods as more fully described below.

DETAILED DESCRIPTION OF PREFERRED EMBODIMENTS

Figure 1:
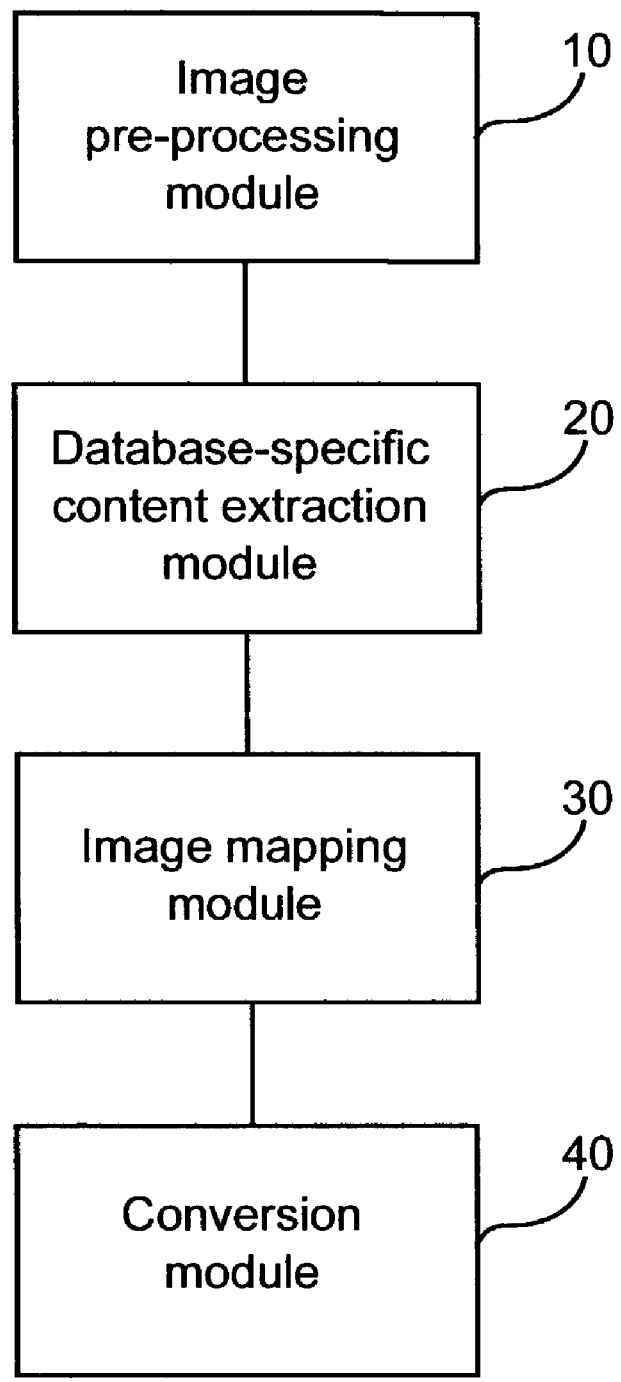
FIG. 1 is a schematic representation of an example architecture provided for converting static images of biological models to editable/modifiable biological models constructed in a local format according to the present invention.

Before the present system, tools and methods are described, it is to be understood that this invention is not limited to particular hardware, steps or commands described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a node" includes a plurality of such nodes and reference to "the model" includes reference to one or more models and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

A "biological model" is defined herein as a visual, graphical representation of a biological or biochemical process. Biological models, as used herein, include, but are not limited to, pathway diagrams, cellular networks, signal transduction pathways, regulatory pathways, metabolic pathways, protein-protein interactions, interactions between molecules, compounds, or drugs, and the like.

An "entity" is defined herein as a subject of interest that a researcher is endeavoring to learn more about. For example, an entity may be a gene, protein, molecule, ligand, disease, drug or other compound, but is not limited to these specific examples.

A "node" as used herein, refers to an entity, which also may be referred to as a "noun" (in a local format, for example). Thus, when data is converted to a local format according to the present invention, nodes are selected as the "nouns" for the local format to build a grammar, language or Boolean logic.

A "link" as used herein, refers to a relationship or action that occurs between entities or nodes (nouns) and may also be referred to as a "verb" (in a local format, for example).

Verbs are identified for use in the local format to construct a grammar, language or Boolean logic. Examples of verbs, but not limited to these, include upregulation, downregulation, inhibition, promotion, bind, cleave and status of genes, protein-protein interactions, drug actions and reactions, etc.

Biological models (pathway diagrams, protein-protein interaction maps, etc.) are great repositories of information related to the current understanding of the functioning of biological processes. With the high-throughput experiments and their results that scientists have to deal with, there is a need to identify information about entities (i.e., genes, proteins, molecules, diseases, drugs, etc.) of interest from existing biological models, and be able to verify/validate these using proprietary experimental results. Although a number of biological model databases have been developed (both public domain and proprietary) that allow users to query and download biological models of interest, once downloaded, they are very difficult for the user to work with. Although they can be readily viewed, they are not editable. Often the user has a very great amount of experimental data that needs to be analyzed/compared, and manual comparison of such data with one or more models is extremely tedious to the point that it is effectively impractical to do with any amount of efficiency.

Biological models may be dependent upon or relate to many different cellular processes, genes, and various expressions of genes with resultant variations in protein abundance. Correlation and testing of data against these models is becoming increasingly more tedious and lengthy with the increased automation of the ways in which gene expression, protein expression, and other data is are generated (e.g., microarrays, RT-PCR, mass spectroscopy, 2-D gels, etc.), and with the consequent increasing complexity and number of models that describe this data. The present invention provides various degrees of automation to facilitate these comparisons, by providing tools and techniques to convert static images of biological models to a local format so that data can be compared with the models (such as by overlaying, editing, etc.) and so that the models can be revised, edited or further develop to improve the understanding of the biological process or processes that it represents. The invention makes use of (manually, semi-automatically or automatically) extracted nodes and links from biological models, which are used to construct an editable model in a local format.

FIG. 1 shows a schematic representation of an example architecture provided for converting static images of biological models to editable/modifiable biological models constructed in a local format. An image preprocessing module 10 converts an image of a biological model into a standard format (for example, JPEG, GIF, PPM, TIFF, Bitmap), such that the image pixels in the converted image can be extracted and further processed. Images to be converted by the preprocessing module may be either digitally created or scanned from a paper source. A comprehensive list of image formats can be found in various sources, including the following web sites: http://www.dcs.ed.ac.uk/home/mxr/gfx/utils-hi.html and http://www.faqs.org/faqs/graphics/file-formats-faq/part3/preamble.html. Moreover, conversion from one format to another is also very common. For example, JAVA 1.4 has an imageio library that handles interchange between a number of commonly used image formats.

Although the biological models to be converted may be graphically complex and vary in format from database to database, each of the models provided within the same database follow a standard/restricted format, i.e., all the symbols used to represent the various entities and relationships are standardized. For this reason, the conversion of the static images within any particular database can be facilitated with reference to the set of constraints or restrictions that are adhered to when the static image is constructed.

In this regard, a database-specific content extraction module 20 is provided. This module stores and can access a set of constraints/restrictions which are peculiar to the database from which the biological model, to be converted, originated. Of course, not all biological models will belong to a set of models having such constraints or rules. An individually created biological model may have such a set of constraints, although these constraints must have been stored in the module 20 in order to take advantage of this aspect of the processing. Thus, although this module is a valuable tool for expediting the processing of a biological model conversion, it is not absolutely necessary in performing an image conversion, and, in some cases, may not be available for processing a biological model.

In most cases involving biological repositories however, module 20 is useful and will have stored those constraints/restrictions (which are often generated by the database as a "legend" which defines these constraints) and module 20 uses these constraints to more easily identify and convert nodes and links meeting the criteria of the stored constraints/restrictions. For example, nouns may be represented as having a particular shape such as a circle or an oval. In such case, the search and identification criteria for any image processing routine is greatly focused, as circles or ovals can be readily identified as nodes. Additional criteria may even be provided, as nodes might also all be colored in a particular color. In this way, an image identification of a blue circle, for example, would increase the confidence of identifying a node, as the process could then also be assured that the letter "O" has not been incorrectly identified as a node if all the text in this type of biological model happened to be in black and was identified as such in the legend.

Similarly, links may be represented as something other than simply a line connecting two or more nodes. For example, a link or reaction may also be identified by a geometrical shape, such as a rectangle or any other shape that would be used consistently throughout the model. Again, color may be used, alternatively, or in addition thereto. When different colors are used for links and nodes, this greatly reduces or eliminates any proximity considerations for identification of the connection of nodes by links (e.g., determining where one begins and the other ends). Further, color coding can greatly reduce or eliminate uncertainty as to whether a node has been identified, or whether it is just something that might look somewhat like a node visually. Subdivisions of nodes and links may also be separately identified by a legend (e.g., one type of node, a ligand is represented as an oval, while another type of node is represented as a circle, with or without separate colors further distinguishing the two). Or, a combination of nodes and links may be represented as a chain of reactions within the overall biological model using another unique identifier in a legend (shape, color, size).

Processing by the database site-specific content extraction module begins with accessing the stored constraints that relate to the particular biological model image that is to be converted. In the case where the image came from a database on the internet, then the HTML address of the image has the name of the database. If the name of the database does not appear on the selected image, then the user can select the database from a list of databases, or a legend from a list of legends. Using the appropriate constraints, image processing proceeds in a much more efficient and accurate manner. For example, if a green circle is identified and the legend referred to defines nodes as green circles, a node can be automatically generated in this situation with a high degree of confidence in its accuracy. In addition to the higher confidence level, this type of conversion requires a great deal less processing capacity than a method of identification which uses approximation techniques requiring many iterations of processing just to determine where a node begins and a link ends, for example. As another example, a legend may identify a link as a yellow line. The module can then easily extract the links as they will be lines having different colors than the nodes, text or other characters in the diagram. Image processing techniques which may be performed by the database-specific content extraction module 20 include one or more of the following: color- and/or shape-processing, morphological analysis (open/close operators), connected component analysis, edge detection, detecting geometrical shapes, template matching, detecting text in the image, etc.) applied to the entire image or regions in the image (which may be pre-selected manually or automatically based on color-processing, shape-processing, and/or connected component analysis).

Another conversion aid which may be used in addition to, or alternatively to the database-specific content extraction module is an image mapping module 30. Some biological models, particularly some of those which are electronically downloaded from the internet, are provided with hyperlinks at various locations on the model indicating areas of interest in a pathway. By clicking on one of these hyperlinks, additional information regarding that location on the pathway of the biological model is accessed. Such information may include location of a particular node or link, name of the entity or reaction represented by the node or link, and/or other more specific information characterizing what it is being represented at that location on the pathway. Image mapping module 30 accesses these hyperlinks and uses the additional information that is accessed to help generate a biological model in a local format.

Additionally, many internet sites or databases associate an image map with the static image of the biological model, wherein links are provided to various entities (nodes) and relations (links) represented in the image. Such information can also be used to aid the process of extraction of objects (such as identifying interesting regions in the image, etc.). Moreover, the hyperlinks and comments in the HTML image map can be used to extract further information, such as details about the genes/proteins of interest, details about various interactions, etc. Those source documents associated with a biological model contain the HTML language that created the image of the associated biological model. For example, when a page is accessed that contains the image of a biological model, by selecting "View" from the toolbar of a browser and then selecting "Source" from the drop down menu that ensues, the HTML language that created the image of the biological model is displayed. Image mapping module 30 also accesses the source of the biological model image and extracts information regarding nodes and links to use in converting the model into an editable form in a local format. The HTML gives coordinates of locations on the map defining the biological model, so that nodes, including specific names of compounds, genes, proteins, and other species of nodes can be textually searched and matched with public databases (such as NCBI Locuslink, UMLS thesaurus, etc.) or a local database that identifies these species as nodes. Similarly, reactions, catalysts, and other varieties of "links" are identified and located by coordinates in the HTML source, which are also extracted for use in creating the local format version of the biological model. The information gained by the image mapping module 30 may also be used to define further restrictions for use in applying image processing and/or OCR techniques by the database-specific content extraction module 20. Alternatively, the image mapping module may be configured to apply image processing and/or OCR techniques based on the information extracted.

Conversion module 40 uses the output of the database-specific content extraction module 20 and/or the image mapping module 30 and any site specific vocabulary (such as provided by a legend or other information document provided by a site or repository) to convert the view of the biological model into a standardized local format. OCR may be further applied to text regions of the static image to convert the text in the image into a machine readable/interpretable/editable format.

The local format used may be a computing language, grammar or Boolean representation of the information having been extracted from the static image and/or source document. As noted above, this information may be further modified or supplemented with additional information, by a user, for example. Local formatting is described in more detail in the commonly owned, copending application Ser. No. 10/154,524 titled "System and Method for Extracting Pre-Existing Data from Multiple Formats and Representing Data in a Common Format for Making Overlays" which is being filed on even date herewith, and which is incorporated by reference herein, in its entirety, by reference thereto. In this way, static images from various sources and which use various criteria to represent the biological models are all converted to a common local formatting which is also editable and modifiable by a user of the local format version.

Additionally, other sources of information relating to the biological models of interest may be converted to the local format and then used for direct comparison with the information in the biological model, used to overlay information onto the local format of the biological model, and or used to supplement or modify the biological model. Sources of such other information include scientific text documents and experimental data. A more detailed description of converting each of these types of data into the local format, as well as processes, techniques and systems for using these various types of information (including overlaying information, inserting one form into another, converting one type to another, etc.) is given in commonly-owned, copending applications Ser. Nos. 10/155,616, 10/155,304 & 10/154,524 entitled "System and Methods for Visualizing Diverse Biological Relationships"; "System, Tools and Methods To Facilitate Identification and Organization of New Information Based on Context of User's Existing Information"; and "System and Method for Extracting Pre-Existing Data from Multiple Formats and Representing Data in a Common Format for Making Overlays" each of which is being filed on even date herewith, and each of which is incorporated by reference herein, in its entirety, by reference thereto.

The present invention provides a mapping from various graphical representations (representations from multiple sources, each using its own format) to the standard local format.

Figure 2:
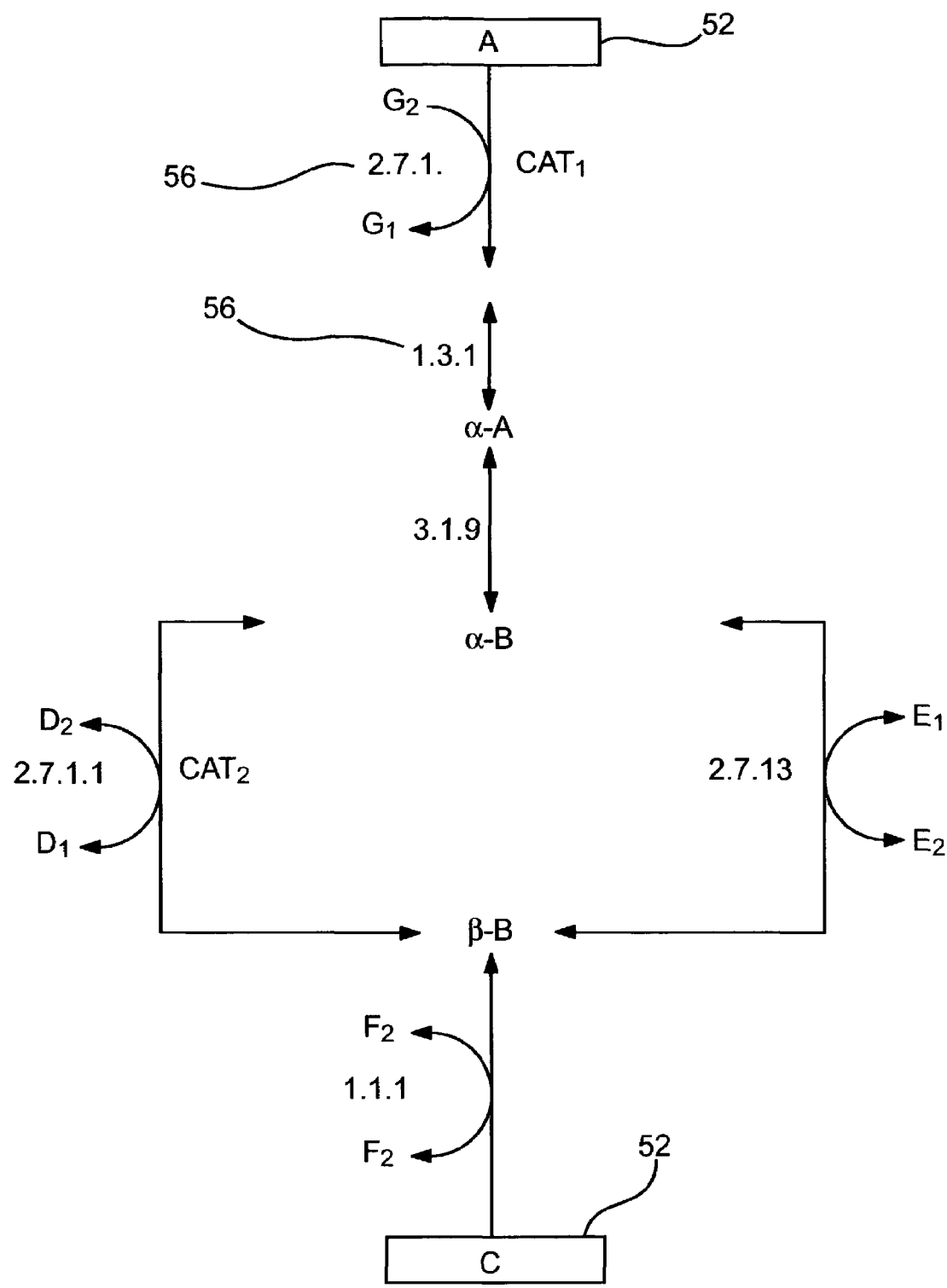
FIG. 2 shows a simplified example of a biological model describing a metabolic pathway.

Referring to FIG. 2, a simplified example of a biological model describing a metabolic pathway is shown. The pathway shown is greatly simplified for clarity of explanation of the principles of the present invention. In practice, pathways of this type are generally much more extensive and complex.

One approach that the present invention employs, as noted above, to automatically, or at least semi-automatically generate a biological model in an editable format (local format) is to employ OCR and other imaging techniques. Image processing module 10 formats the image to into a standard format (for example, JPEG, PBM, Bitmap), shown in FIG. 2, such that the image pixels in the converted image can be extracted and further processed.

In this example, the starting and final products in the biological model are located in rectangular boxes 52, which would be noted in the legend provided with the biological model. Additionally, all compounds (or nodes) (i.e., A, $\alpha$-A, $\alpha$-B, $\alpha$-B, C, D1, D2, E1, E2, F1, F2, G1, and G2) are entered in blue colored text in this model. Catalysts (CAT1 and CAT2) are represented in a green font, and the links (verbs or reaction lines) are represented by red lines, with arrow heads indicating a direction in which the reaction takes place. All of this color coding would be included in a legend and would greatly facilitate the processing of this image by database-specific content extraction module 20, which stores all of the legend information and uses it to readily identify the components of the pathway, their names and locations. In this case, a link is easily identified and located by merely defining the extent of a red line, for example. Well-known imaging techniques can identify such lines and their colors as well as the arrowheads. The same holds true for identification and location placement of the nodes (nouns) and catalysts. All of this information is readily extracted by module 20 to be inputted to conversion module 40 for use in making the locally formatted image.

Still further, the numbers 56 in FIG. 2 are represented in still another color (such as yellow, for example) and are hyperlinks that can access further information detailing what is occurring in the location where that particular number appears. Module 30 can identify these hyperlinks using the color coding contained in the site-specific information stored in the module, and image mapping module 30 accesses the hyperlinks and extracts the additional information about each node or link, etc. This additional information is also inputted to conversion module 40 which may use the information in constructing the local formatted model or at least link the information (in the local format) to an appropriate location of the locally formatted model.

Figure 3:
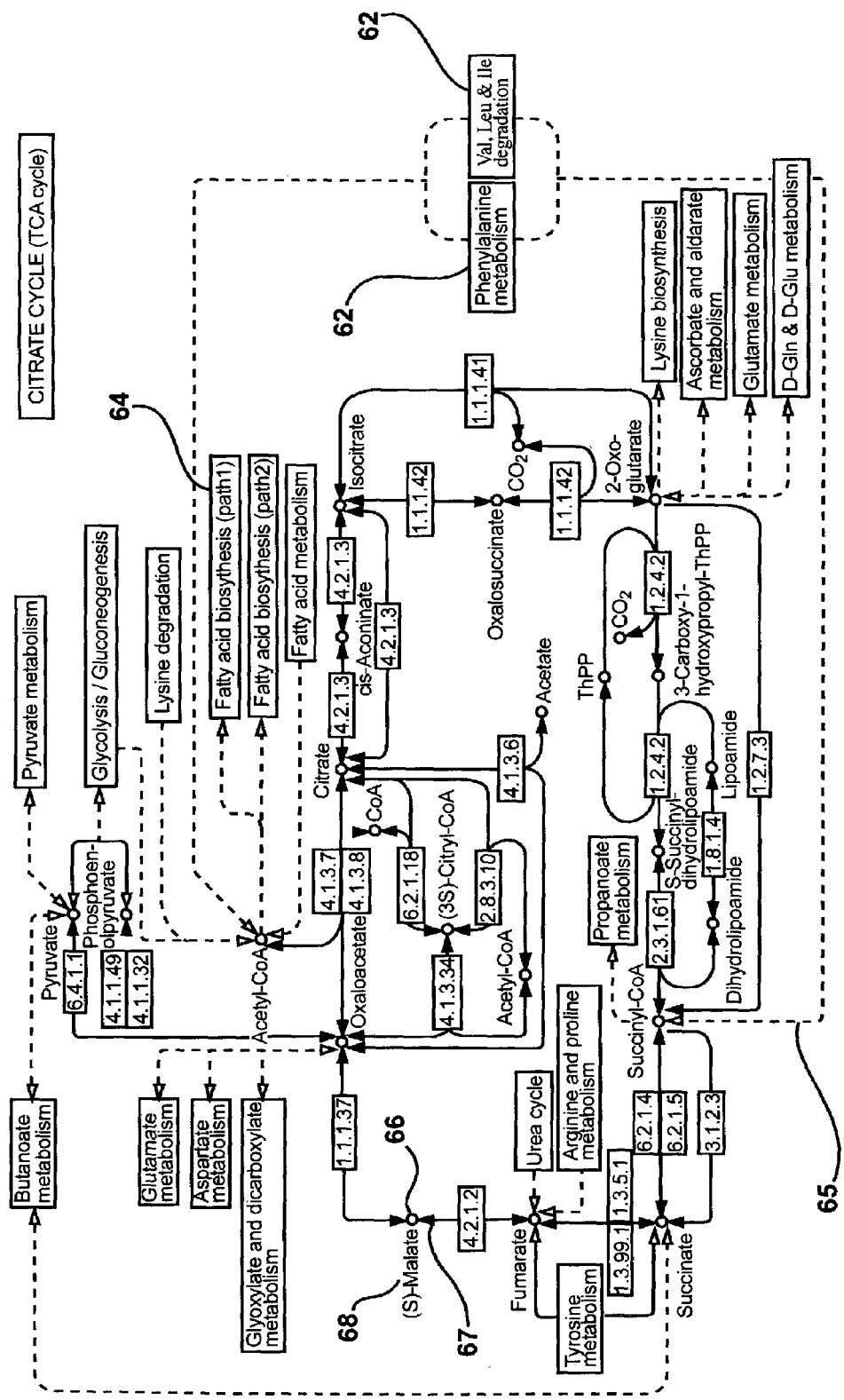
FIG. 3 shows an example of a pathway diagram of a citrate cycle.

FIG. 3 shows an example of a pathway diagram from KEGG (www.genome.ad.jp/kegg/pathway/map/map00020.html) which is an image of a citrate cycle. This image is not color coded. However, reactions are represented as rectangular boxes 62, whereas larger processes (which may have a set of reactions within) are represented in oval boxes 64. Inputs and outputs to various reactions are represented as small circles 66, with text 68 in the vicinity representing the biological substrate. Arrows represent the progress of reactions, with solid arrows 67 representing other reactions and dashed arrows 65 representing other processes (which would encode multiple reactions).

Table 1 below contains HTML-based image map data excerpted from the source document associated with the biological model shown in FIG. 3:

TABLE 1

```
<map name="mapdata">
<area shape=rect coords=114,478,160,495   href="/dbget-bin/www_bget?enzyme+1.3.99.1"
    onMouseOver="note('enzyme: 1.3.99.1');return true" onMouseOut="clr()">
<area shape=rect coords=484,47,607,72   href="/kegg/pathway/map/map00620.html"
    onMouseOver="note('map00620.html');return true" onMouseOut="clr()">
<area shape=rect coords=478,583,523,600   href="/dbget-bin/www_bget?enzyme+1.2.7.3"
    onMouseOver="note('enzyme: 1.2.7.3');return true" onMouseOut="clr()">
<area shape=rect coords=420,548,465,565   href="/dbget-bin/www_bget?enzyme+1.8.1.4"
    onMouseOver="note('enzyme: 1.8.1.4');return true" onMouseOut="clr()">
```

TABLE 1-continued

```
<area shape=rect coords=613,509,658,526    href="/dbget-bin/www_bget?enzyme+1.2.4.2"
    onMouseOver="note('enzyme: 1.2.4.2');return true" onMouseOut="clr()">
<area shape=rect coords=478,509,523,526    href="/dbget-bin/www_bget?enzyme+1.2.4.2"
    onMouseOver="note('enzyme: 1.2.4.2');return true" onMouseOut="clr()">
<area shape=rect coords=355,509,400,526    href="/dbget-bin/www_bget?enzyme+2.3.1.61"
    onMouseOver="note('enzyme: 2.3.1.61');return true" onMouseOut="clr()">
<area shape=rect coords=212,520,257,537    href"/dbget-bin/www_bget?enzyme+6.2.1.5"
    onMouseOver="note('enzyme: 6.2.1.5');return true" onMouseOut="clr()">
<area shape=rect coords=212,499,257,516    href="/dbget-bin/www_bget?enzyme+6.2.1.4"
    onMouseOver="note('enzyme: 6.2.1.4');return true" onMouseOut"clr()">
<area shape=rect coords=674,442,719,459    href="/dbget-bin/www_bget?enzyme+1.1.1.42"
    onMouseOver="note('enzyme: 1.1.1.42');return true" onMouseOut="clr()">
<area shape=rect coords=754,381,799,398    href="/dbget-bin/www_bget?enzyme+1.1.1.41"
    onMouseOver="note('enzyme: 1.1.1.41');return true" onMouseOut"clr()">
<area shape=rect coords=675,337,720,354    href="/dbget-bin/www_bget?enzyme+1.1.1.42"
    onMouseOver="note('enzyme: 1.1.1.42');return true" onMouseOut"clr()">
<area shape=rect coords=574,313,619,330    href="/dbget-bin/www_bget?enzyme+4.2.1.3"
    onMouseOver="note('enzyme: 4.2.1.3');return true" onMouseOut="clr()">
<area shape=rect coords=476,402,521,419    href="/dbget-bin/www_bget?enzyme+4.1.3.6"
    onMouseOver="note('enzyme: 4.1.3.6');return true" onMouseOut="clr()">
<area shape=rect coords=389,385,434,402    href="/dbget-bin/www_bget?enzyme+2.8.3.10"
    onMouseOver="note('enzyme: 2.8.3.10');return true" onMouseOut"clr()">
<area shape=rect coords=389,329,434,347    href="/dbget-bin/www_bget?enzyme+6.2.1.18"
    onMouseOver="note('enzyme: 6.2.1.18');return true" onMouseOut="clr()">
<area shape=rect coords=386,290,431,307    href="/dbget-bin/www_bget?enzyme+4.1.3.8"
    onMouseOver="note('enzyme: 4.1.3.8');return true" onMouseOut="clr()">
<area shape=rect coords=310,357,355,374    href="/dbget-bin/www_bget?enzyme+4.1.3.34"
    onMouseOver="note('enzyme: 4.1.3.34');return true" onMouseOut="clr()">
<area shape=rect coords=164,478,209,495    href="/dbget-bin/www_bget?enzyme+1.3.5.1"
    onMouseOver="note('enzyme: 1.3.5.1');return true" onMouseOut="clr()">
<area shape=rect coords=143,371,188,388    href="/dbget-bin/www_bget?enzyme+4.2.1.2"
    onMouseOver="note('enzyme: 4.2.1.2');return true" onMouseOut="clr()">
<area shape=rect coords=622,280,667,297    href="/dbget-bin/www_bget?enzyme+4.2.1.3"
    onMouseOver="note('enzyme: 4.2.1.3');return true" onMouseOut="clr()">
<area shape=rect coords=523,280,568,297    href="/dbget-bin/www_bget?enzyme+4.2.1.3"
    onMouseOver="note('enzyme: 4.2.1.3');return true" onMouseOut="clr()">
<area shape=rect coords=386,269,431,286    href="/dbget-bin/www_bget?enzyme+4.1.3.7"
    onMouseOver="note('enzyme: 4.1.3.7');return true" onMouseOut="clr()">
<area shape=rect coords=205,280,250,297    href="/dbget-bin/www_bget?enzyme+1.1.1.37"
    onMouseOver="note('enzyme: 1.1.1.37');return true" onMouseOut="clr()">
<area shape=rect coords=317,83,362,100    href="/dbget-bin/www_bget?enzyme+6.4.1.1"
    onMouseOver="note('enzyme: 6.4.1.1');return true" onMouseOut="clr()">
<area shape=rect coords=317,132,362,149    href="/dbget-bin/www_bget?enzyme+4.1.1.32"
    onMouseOver="note('enzyme: 4.1.1.32');return true" onMouseOut="clr()">
<area shape=rect coords=317,111,362,128    href="/dbget-bin/www_bget?enzyme+4.1.1.49"
    onMouseOver="note('enzyme: 4.1.1.49');return true" onMouseOut="clr()">
<area shape=rect coords=94,212,252,246    href="/kegg/pathway/map/map00630.html"
    onMouseOver="note('map00630.html');return true" onMouseOut="clr()">
<area shape=rect coords=484,98,641,123    href="/kegg/pathway/map/map00010.html"
    onMouseOver="note('map00010.html');return true" onMouseOut="clr()">
<area shape=rect coords=536,189,702,214    href="/kegg/pathway/map/map00061.html"
    onMouseOver="note('map00061.html');return true" onMouseOut="clr()">
<area shape=rect coords=536,217,702,242    href="/kegg/pathway/map/map00062.html"
    onMouseOver="note('map00062.html');return true" onMouseOut="clr()">
<area shape=rect coords=577,245,702,270    href="/kegg/pathway/map/map00071.html"
    onMouseOver="note('map00071.html');return true" onMouseOut="clr()">
<area shape=rect coords=367,468,443,502    href="/kegg/pathway/map/map00640.html"
    onMouseOver="note('map00640.html');return true" onMouseOut="clr()">
<area shape=rect coords=771,536,897,571    href="/kegg/pathway/map/map00053.html"
    onMouseOver="note('map00053.html');return true" onMouseOut="clr()">
<area shape=rect coords=772,574,898,600    href="/kegg/pathway/map/map00251.html"
    onMouseOver="note('map00251.html');return true" onMouseOut="clr()">
<area shape=rect coords=174,136,252,170    href"/kegg/pathway/map/map00251.html"
    onMouseOver="note('map00251.html');return true" onMouseOut"clr()">
<area shape=rect coords=754,53,966,80    href="/dbget-bin/get_linkdb?pathway+map00020"
    onMouseOver="note('pathway: map00020');return true" onMouseOut"clr()">
<area shape=rect coords=175,43,251,77    href="/kegg/pathway/map/map00650.html"
    onMouseOver="note('map00650.html');return true" onMouseOut="clr()">
<area shape=rect coords=848,383,932,417    href="/kegg/pathway/map/map00360.html"
    onMouseOver="note('map00360.html');return true" onMouseOut="clr()">
<area shape=rect coords=53,442,129,476    href="/kegg/pathway/map/map00350.html"
    onMouseOver"note('map00350.html');return true" onMouseOut="clr()">
<area shape=rect coords=533,144,644,169 href="/kegg/pathway/map/map00310.html"
    onMouseOver="note('map00310.html');return true" onMouseOut="clr()">
<area shape=rect coords=783,508,895,533    href="/kegg/pathway/map/map00300.html"
    onMouseOver="note('map00300.html');return true" onMouseOut="clr()">
<area shape=rect coords=936,383,1021,417 href="/kegg/pathway/map/map00280.html"
    onMouseOver="note('map00280.html');return true" onMouseOut="clr()">
```

TABLE 1-continued

```
<area shape=rect coords=174,174,252,208 href="/kegg/pathway/map/map00252.html"
    onMouseOver="note('map00252.html');return true" onMouseOut="clr()">
<area shape=rect coords=202,442,318,476 href="/kegg/pathway/map/map00330.html"
    onMouseOver="note('map00330.html');return true" onMouseOut="clr()">
<area shape=rect coords=201,414,269,440    href="/kegg/pathway/map/map00220.html"
    onMouseOver="note('map00220.html');return true" onMouseOut="clr()">
<area shape=rect coords=772,603,924,629    href="/kegg/pathway/map/map00471.html"
    onMouseOver="note('map00471.html');return true" onMouseOut="clr()">
<area shape=rect coords=212,547,257,564    href="/dbget-bin/www_bget?enzyme+3.1.2.3"
    onMouseOver="note('enzyme: 3.1.2.3');return true" onMouseOut="clr()">
<area shape=circle    coords=390,91,4    href="/dbget-bin/www_bget?compound+C00022"
    onMouseOver="note('compound: C00022');return true"    onMouseOut="clr()">
<area shape=circle    coords=165,425,4    href="/dbget-
    bin/www_bget?compound+C00122"
    onMouseOver="note('compound: C00122');return true"    onMouseOut="clr()">
<area shape=circle    coords=295,288,4    href="/dbget-
    bin/www_bget?compound+C00036"
    onMouseOver="note('compound: C00036');return true"    onMouseOut="clr()">
<area shape=circle    coords=697,401,4    href="/dbget-
    bin/www_bget?compound+C05379"
    onMouseOver="note('compound: C05379');return true"    onMouseOut="clr()">
<area shape=circle    coords=390,130,4    href="/dbget-
    bin/www_bget?compound+C00074"
    onMouseOver="note('compound: C00074');return true"    onMouseOut="clr()">
<area shape=circle    coords=370,229,4    href="/dbget-
    bin/www_bget?compound+C00024"
    onMouseOver="note('compound: C00024');return true"    onMouseOut="clr()">
<area shape=circle    coords=165,337,4    href="/dbget-
    bin/www_bget?compound+C00149"
    onMouseOver="note('compound: C00149');return true"    onMouseOut="clr()">
<area shape=circle    coords=693,288,4    href="/dbget-
    bin/www_bget?compound+C00311"
    onMouseOver="note('compound: C00311');return true"    onMouseOut="clr()">
<area shape=circle    coords=596,288,4    href="/dbget-
    bin/www_bget?compound+C00417"
    onMouseOver"note('compound: C00417');return true"    onMouseOut="clr()">
<area shape=circle    coords=162,518,4    href="/dbget-
    bin/www_bget?compound+C00042"
    onMouseOver="note('compound: C00042');return true"    onMouseOut="clr()">
<area shape=circle    coords=378,365,4    href="/dbget-
    bin/www_bget?compound+C00566"
    onMouseOver="note('compound: C00566');return true"    onMouseOut="clr()">
<area shape=circle    coords=453,312,4    href="/dbget-
    bin/www_bget?compound+C00010"
    onMouseOver="note('compound: C00010');return true"    onMouseOut="clr()">
<area shape=circle    coords=497,288,4    href="/dbget-
    bin/www_bget?compound+C00158"
    onMouseOver="note('compound: C00158);return true"    onMouseOut="clr()">
<area shape=circle    coords=498,557,4    href="/dbget-
    bin/www_bget?compound+C00248"
    onMouseOver="note('compound C00248');return true"    onMouseOut="clr()">
<area shape=circle    coords=566,478,4    href="/dbget-
    bin/www_bget?compound+C00068"
    onMouseOver="note('compound: C00068');return true"    onMouseOut="clr()">
<area shape=circle    coords=345,420,4    href="/dbget-
    bin/www_bget?compound+C00024"
    onMouseOver="note('compound: C00024');return true"    onMouseOut="clr()">
<area shape=circle    coords=[]437,518,4    href="/dbget-
    bin/www_bget?compound+C01169"
    onMouseOver="note('compound: C01169');return true"    onMouseOut="clr()">
<area shape=circle    coords=383,557,4    href="/dbget-
    bin/www_bget?compound+C00579"
    onMouseOver="note('compound: C00579');return true"    onMouseOut="clr()">
<area shape=circle    coords=309,518,4    href="/dbget-
    bin/www_bget?compound+C00091"
    onMouseOver="note('compound C00091');return true"    onMouseOut="clr()">
<area shape=circle    coords=736,417,4    href="/dbget-
    bin/www_bget?compound+C00011"
    onMouseOver="note('Compound C00011');return true"    onMouseOut="clr()">
<area shape=circle    coords=697,517,4    href="/dbget-
    bin/www_bget?compound+C00026"
    onMouseOver="note('Compound C00026');return true"    onMouseOut="clr()">
<area shape=circle    coords=595,490,4    href="/dbget-
    bin/www_bget?compound+C00011"
    onMouseOver="note('compound C00011');return true"    onMouseOut="clr()">
<area shape=circle    coords=567,517,4    href="/dbget-
    bin/www_bget?compound+C05381"
    onMouseOver="note('Compound C05381');return true"    onMouseOut="clr()">
```

TABLE 1-continued

```
<area shape=circle    coords=539,433,4    href="/dbget-
   bin/www_bget?compound+C00033"
      onMouseOver="note('compound: C00033');return true"    onMouseOut="clr()">
</map>
```

Image mapping module 30 accesses the map data associated with the biological model and extracts information relevant to the links and nodes represented in the biological model, as well as any other entities that may be of interest in constructing a version of the biological model in the local format. For example, module 30 extracts the shape of pertinent objects in the map, e.g., "shape=rect", the coordinates of that shape: "coords=114, 478, 160, 495" and the characterization of that entity "enzyme", all of which will be used by conversion module 40 in constructing the locally formatted model. Each line of the map is extracted in this way.

Figure 4:
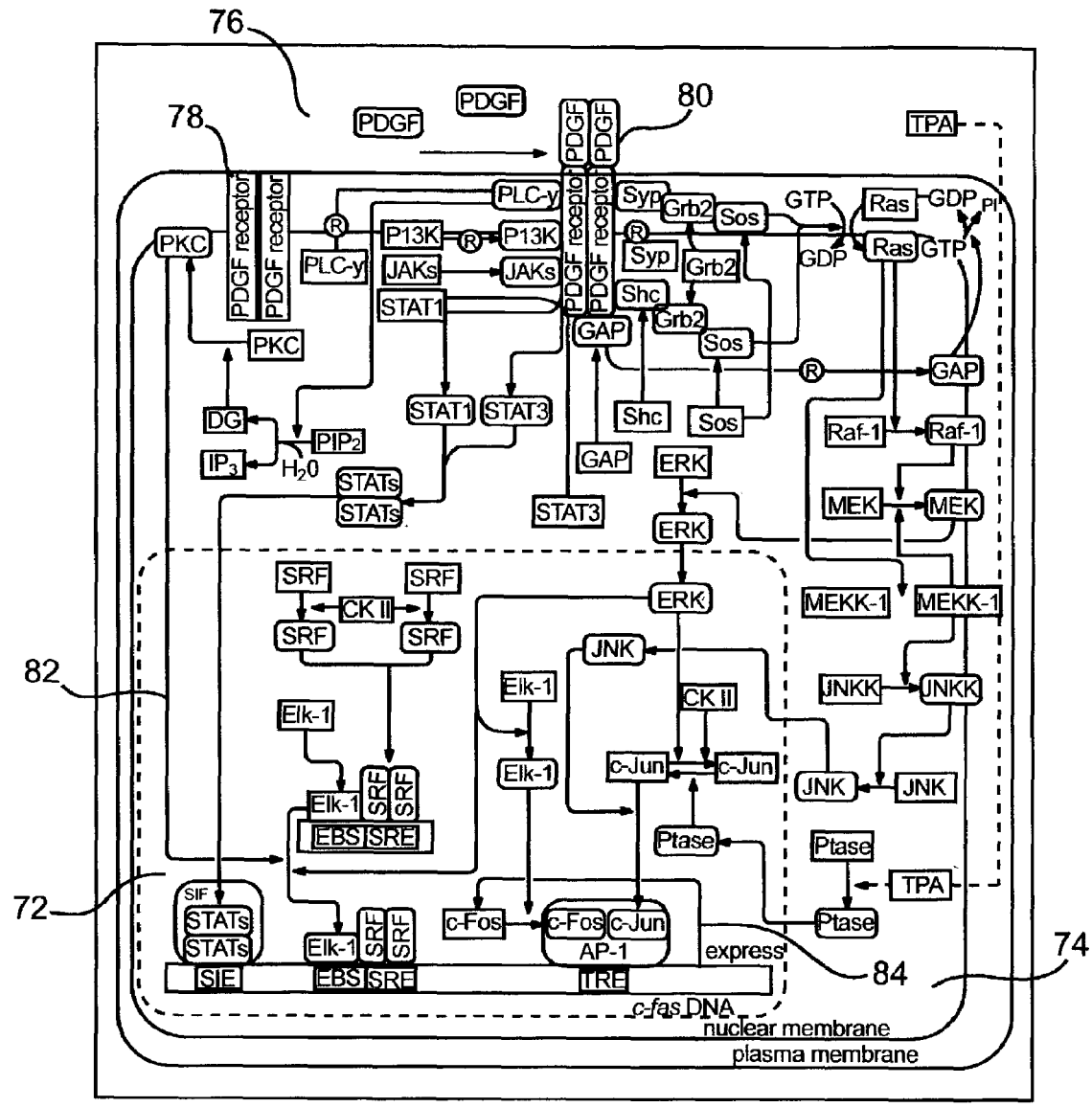
FIG. 4 shows an example of a biological model representing a signal transduction pathway.

FIG. 4 visually represents a signal transduction pathway. Color and shape are again used in a standard format in all pathway diagrams from this database (legend is described at http://www.art.kvushu-u.ac.ip/spad/legend.html). Color coding is used to represent the nucleus 72 (e.g., colored pink), cytoplasm 74 (e.g., colored yellow), and extra-cellular regions 76 (e.g., colored white). Variations in the shape of the boxes suggest different types of molecules, receptors, etc. (e.g., receptor 78, ligand 80, and so on). Additionally, the differently shaped boxes may also be colored differently. For example, in this diagram, ligands 80 are colored orange and receptors 78 are colored green. Arrows 82 represent progress of a signal along the pathway and are colored black, except for a gene expression relationship 84 (leads to expression of gene) which is colored red.

In this example, a great deal of image processing using the database-specific content extraction module 20 can be accomplished. Colors can be used to identify not only nodes and links, but types of nodes (e.g., ligand, receptor, etc.) as well as types of links (e.g., normal conduction relationship 82, gene expression event 84). Further, color can be used to spatially identify the nucleus of the cell, the protoplasm of the cell and extracellular regions. This spatial information may or may not be used to create the locally formatted biological model, depending upon the complexity of the model to be constructed and information from other sources that the user intends to compare, overlay or edit the biological model with. In any event, the spatial information can be stored in the local format as part of the total information associated with the biological model constructed, and is in this way equally accessible to the user for comparisons, modifications, etc.

The arrows 82 and 84 can be readily identified using image processing techniques in combination with knowledge of the color encoding of the same. The same goes for the nodes, and the boundaries between the nodes are readily identified by differences between the colors of the nodes and the links.

Additionally, the image mapping module 30 can be used for extracting important information from the model of FIG. 4 in the same way described above with regard to FIG. 3. Table 2 below shows an excerpt of the HTML-based image map data contained in the source document associated with the biological model shown in FIG. 4:

TABLE 2

```
<HTML>
<title>Signaling Pathway: PDGF</tftle>
<body bgcolor="#eeeeee">
<center>
<h2>Signaling Pathway mediated by PDGF</h2>
<hr>
<b>
This is a clickable map. Please click on a factor to go to spad information.
</bxp>
<img src="Jmages/signalpathway/pdgf.gif" usemap="#PDGF"
width=616height=678xp>
<map name="PDGF">
<!-PDGF_left->
<area shape="rect" coords="171,27 206,46"    href=".7account/ligand/pdgf.html">
<!-PDGF_right->
<area shape="rect" coords="240,11 275,30"    href='Jaccount/ligand/pdgf.html">
<!-PDGF_comp-->
<area shape="rect" coords="305,30 341,65"    href=".Vaccount/ligand/pdgf.html">
<!~PDGFreceptor_inactive_left->
<area shape="rect" coords="80,69 99,140"    href=".7account/receptor/pdgfr.html">
<!-PDGFreceptor_inactive_right->
```

The information extracted from the HTML image map is inputted to the conversion module 40 which uses the information to construct a model in the local format which is editable by the user, who can then modify or supplement the model, perform overlays on the model, and the like.

Given the standard format of images (graphics) from a particular database source, the present processing system can convert a static image into an editable pathway diagram relatively efficiently compared to image processing techniques that do not rely upon any additional data. Although the processes above have been described relative to fixed database sources, such as KEGG and SPAD, the present invention can be easily extended to other database sources.

The present invention may perform all of the above processes automatically or semi-automatically. For example, user input is also allowed. If, upon reviewing a model in the local format, a user discovers an error, or wants to modify the model in some way, manual editing of the model is allowed.

Using the present invention, a user can import biological models and convert the static images that represent these models into editable models. The transformation to a common local format allows multiple models to be linked together and also to link/relate biological models to other types of data, such as scientific text, experimental results, interpretations, etc., as noted above.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of extracting semantics from a static graphic image of a biological model of a biological or biochemical process, and for converting the static image to an editable biological model of the biological or biochemical process, said method comprising the steps of:
   accessing stored information defining predefined constraints used to create the static image;
   identifying at least one entity or relationship represented in the static image, based upon the stored information;
   extracting, from the stored information, information describing the at least one entity or relationship; and
   converting at least a portion of the biological model to an editable, local format using the extracted information.

2. The method of claim 1, wherein the predefined constraints are site-specific vocabulary.

3. The method of claim 1, wherein the predefined constraints include assignments of different colors to entities and relationships, and said identifying includes color processing of the static image.

4. The method of claim 1, wherein the predefined constraints include assignments of different shapes to entities and relationships, and said identifying includes template matching.

5. The method of claim 1, wherein the static image is digitally created or scanned from a paper source, said method further comprising the step of converting the static image into a standard format prior to the identifying and extracting steps.

6. The method of claim 5, wherein the standard format is selected from the group consisting of JPEG, PBM, GIF, PPM, TIFF and Bitmap.

7. The method of claim 1, further comprising the steps of:
   accessing an image map used to create the static image;
   identifying at least one entity or relationship represented in the static image, based upon information in the image map;
   extracting information describing the at least one entity or relationship identified based upon the image map information; and
   converting at least a portion of the biological model to the editable, local format using the information extracted based upon the image map information.

8. The method of claim 7 wherein the image map comprises HTML.

9. The method of claim 1, further comprising the step of manually converting at least a portion of the biological model to an editable, local format.

10. A method of extracting semantics from a static graphic image of a biological model of a biological or biochemical process, and for converting the static image to an editable biological model of a biological or biochemical process, said method comprising the steps of:
   accessing an image map used to create the static image;
   identifying at least one entity or relationship represented in the static image, based upon information in the image map;
   extracting information describing the at least one entity or relationship; and
   converting at least a portion of the biological model to the editable, local format using the extracted information.

11. The method of claim 10, wherein the image map comprises HTML.

12. The method of claim 10, wherein the static image is digitally created or scanned from a paper source, said method further comprising the step of converting the static image into a standard format prior to the identifying and extracting steps.

13. The method of claim 12, wherein the standard format is selected from the group consisting of JPEG, PBM, GIF, TIFF, PPM, and Bitmap.

14. The method of claim 10, further comprising the steps of:
   accessing stored information defining predefined constraints used to create the static image;
   identifying at least one entity or relationship represented in the static image, based upon the stored information;
   extracting information describing the at least one entity or relationship, based upon the stored information; and
   converting at least a portion of the biological model to an editable, local format using the information that was extracted based upon the stored information.

15. The method of claim 10, further comprising the step of manually converting at least a portion of the biological model to an editable, local format.

16. A method of extracting semantics from a static graphic image of a biological model and for converting the static image to an editable biological model, said method comprising the steps of:
   converting the static image to a standard format:
   extracting information from the standard formatted static image using image processing based upon content defining specific constraints on the static image; and
   mapping the extracted information according to a local format, thereby making an editable map.

17. The method of claim 16, wherein the image processing used in the extracting step includes one or more of the techniques selected from the group consisting of: color processing, shape processing, morphological analysis with open operators, morphological analysis with closed operators, connected component analysis, edge detection, detecting geometrical shapes, template matching and text detection.

18. The method of claim 16, wherein the method is applied to the entire static image.

19. The method of claim 16, wherein the method is applied to manually preselected regions of the static image.

20. The method of claim 16, wherein the method is applied to automatically preselected regions of the static image.

21. The method of claim 20, wherein the automatically preselected regions are selected based upon at least one of color-processing, shape-processing, and connected component analysis.

22. The method of claim 16, wherein the content defining specific constraints on the static image is site-specific content.

23. The method of claim 16, further comprising the steps of:
  extracting other information relating to the static image;
  converting the other information to the local format; and
  mapping at least a portion of the locally formatted information on the editable map or linking the other information in the local format to the editable map.

24. The method of claim 23, wherein the other information comprises HTML tags on the static image map.

25. The method of claim 23, wherein the other information comprises information in an image map used to create the static image.

26. The method of claim 16, further comprising the step of applying OCR to text regions of the static image to convert the text to the local format.

27. A system for extracting semantics from a static graphic image of a biological model of a biological or biochemical process, and for converting the static image to an editable biological model of a biological or biochemical process, said system comprising:
  means for accessing stored information defining predefined constraints used to create the static image;
  means for identifying at least one entity or relationship represented in the static image, based upon the stored information;
  means for extracting information describing the at least one entity or relationship; and
  means for converting at least a portion of the biological model to an editable, local format using the extracted information.

28. The system of claim 27, further comprising:
  means for converting the static image into a standard format prior to extracting semantics therefrom.

29. The system of claim 27, further comprising:
  means for accessing an image map used to create the static image;
  means for identifying at least one entity or relationship represented in the static image, based upon information in the image map;
  means for extracting information describing the at least one entity or relationship identified based upon the image map information; and
  means for converting at least a portion of the biological model to the editable, local format using the information extracted based upon the image map information.

30. The method of claim 27, further comprising means for manually converting at least a portion of the biological model to an editable, local format.

31. A system for extracting semantics from a static graphic image of a biological model of a biological or biochemical process, and for converting the static image to an editable biological model of a biological or biochemical process, said system comprising:
  a database-specific content extraction module adapted to extract content from the static image based on predefined constraints specific to a database from which the static image originated; and
  a conversion module adapted to convert the extracted content to a local format used to create an editable biological map corresponding to the static image of the biological model of the biological or biochemical process.

32. The system of claim 31, further comprising an image mapping module adapted to extract content in or relating to the static image, based upon an image map, and input the extracted content from or relating to the static image to the conversion module.

33. The system of claim 31, further comprising an image pre-processing module adapted to convert the static image to a standard format, prior to further processing by the system.

34. A computer readable medium carrying one or more sequences of instructions from a user of a computer system for extracting semantics from a static graphic image of a biological model of a biological or biochemical process, and for converting the static image to an editable biological model of a biological or biochemical process, wherein the execution of the one or more sequences of instructions by one or more processors cause the one or more processors to perform the steps of:
  accessing stored information defining predefined constraints used to create the static image of biological model of the biological or biochemical process;
  identifying at least one entity or relationship represented in the static image, based upon the stored information;
  extracting information describing the at least one entity or relationship; and
  converting at least a portion of the biological model to an editable, local format using the extracted information.

35. The computer readable medium of claim 34, wherein the static image is digitally created or scanned from a paper source, wherein the following further step is performed:
  converting the static image into a standard format prior to the identifying and extracting steps.

36. The computer readable medium of claim 34, wherein the following further steps are performed:
  accessing an image map used to create the static image;
  identifying at least one entity or relationship represented in the static image, based upon information in the image map;
  extracting information describing the at least one entity or relationship identified based upon the image map information; and
  converting at least a portion of the biological model to the editable, local format using the information extracted based upon the image map information.

37. A computer readable medium carrying one or more sequences of instructions from a user of a computer system for extracting semantics from a static graphic image of a biological model of a biological or biochemical process, and for converting the static image to an editable biological model of a biological or biochemical process, wherein the execution of the one or more sequences of instructions by one or more processors cause the one or more processors to perform the steps of:
  accessing an image map used to create the static image of the biological model of the biological or biochemical process;
  identifying at least one entity or relationship represented in the static image, based base upon information in the image map;
  extracting information describing the at least one entity or relationship; and
  converting at least a portion of the biological model to the editable, local format using the extracted information.

* * * * *